US012636075B2

(12) United States Patent
Altmann et al.

(10) Patent No.: US 12,636,075 B2
(45) Date of Patent: May 26, 2026

(54) METHOD AND SYSTEM FOR CALCULATING AND UTILIZING PFA ABLATION INDEX

(71) Applicant: BIOSENSE WEBSTER (ISRAEL) LTD., Yokneam (IL)

(72) Inventors: Andres Claudio Altmann, Haifa (IL); Liran Schwartz, Kiryat Motzkin (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 380 days.

(21) Appl. No.: 18/212,383

(22) Filed: Jun. 21, 2023

(65) Prior Publication Data

US 2025/0000573 A1      Jan. 2, 2025

(51) Int. Cl.
A61B 18/14          (2006.01)
A61B 18/00          (2006.01)

(52) U.S. Cl.
CPC ..................... *A61B 18/1492* (2013.01); *A61B 2018/00351* (2013.01); *A61B 2018/00577* (2013.01); *A61B 2018/00613* (2013.01); *A61B 2018/00642* (2013.01); *A61B 2018/00773* (2013.01)

(58) Field of Classification Search
CPC .......... A61B 2018/00351; A61B 2018/00577; A61B 2018/00613; A61B 2018/00636; A61B 2018/00642; A61B 2018/00648; A61B 2018/00654; A61B 2018/00773; A61B 18/1492
See application file for complete search history.

(56) References Cited

U.S. PATENT DOCUMENTS

| | | | |
|---|---|---|---|
| 5,391,199 | A | 2/1995 | Shlomo |
| 5,443,489 | A | 8/1995 | Ben-Haim |
| 5,558,091 | A | 9/1996 | Acker |
| 6,172,499 | B1 | 1/2001 | Ashe |
| 6,239,724 | B1 | 5/2001 | Doron |
| 6,332,089 | B1 | 12/2001 | Acker |
| 6,484,118 | B1 | 11/2002 | Govari |
| 6,618,612 | B1 | 9/2003 | Acker |
| 6,690,963 | B2 | 2/2004 | Ben-Haim |
| 6,788,967 | B2 | 9/2004 | Ben-Haim |

(Continued)

FOREIGN PATENT DOCUMENTS

| | | |
|---|---|---|
| EP | 4450010 A1 | 10/2025 |
| WO | WO2023/009586 A1 | 2/2023 |

OTHER PUBLICATIONS

European Search Report for corresponding EPA No. 24183258.3 dated Nov. 22, 2024.

*Primary Examiner* — Bradford C. Blaise

(57)          ABSTRACT

A method, apparatus and computer program product, the method comprising receiving input from a force sensor on a catheter, the catheter comprising electrodes for ablating a heart of a patient, the catheter placed at a location within the heart; based at least on the received input, calculating a predicted PFA ablation index (PFA AI) of an ablation that would be caused by applying by the catheter force equal to the assessment at the location for a predetermined number of electrical pulses having predetermined magnitude and predetermined duration, wherein said calculation is in accordance with a predefined formula; and displaying the predicted PFA AI to a user of the catheter.

14 Claims, 4 Drawing Sheets

(56)             References Cited

U.S. PATENT DOCUMENTS

| | | | |
|---|---|---|---|
| 6,892,091 | B1 | 5/2005 | Ben-Haim |
| 7,536,218 | B2 | 5/2009 | Govari et al. |
| 7,756,576 | B2 | 7/2010 | Levin |
| 7,848,787 | B2 | 12/2010 | Osadchy |
| 7,869,865 | B2 | 1/2011 | Govari et al. |
| 8,456,182 | B2 | 6/2013 | Bar-Tal et al. |
| 8,676,305 | B2 | 3/2014 | Hayam et al. |
| 9,629,567 | B2 | 4/2017 | Porath et al. |
| 2010/0069921 | A1* | 3/2010 | Miller ................ A61B 18/1233 |
| | | | 600/301 |
| 2014/0100563 | A1* | 4/2014 | Govari ............... A61B 18/1492 |
| | | | 606/41 |
| 2015/0088120 | A1* | 3/2015 | Garcia ............... A61B 18/1477 |
| | | | 606/34 |
| 2017/0014181 | A1* | 1/2017 | Bar-Tal ............. A61B 18/1492 |
| 2017/0319279 | A1* | 11/2017 | Fish ....................... A61B 18/12 |
| 2021/0186604 | A1 | 6/2021 | Altmann |
| 2024/0252234 | A1* | 8/2024 | Razon ................... G06N 20/00 |
| 2025/0143781 | A1* | 5/2025 | Falahatpisheh .... A61B 18/1492 |

\* cited by examiner

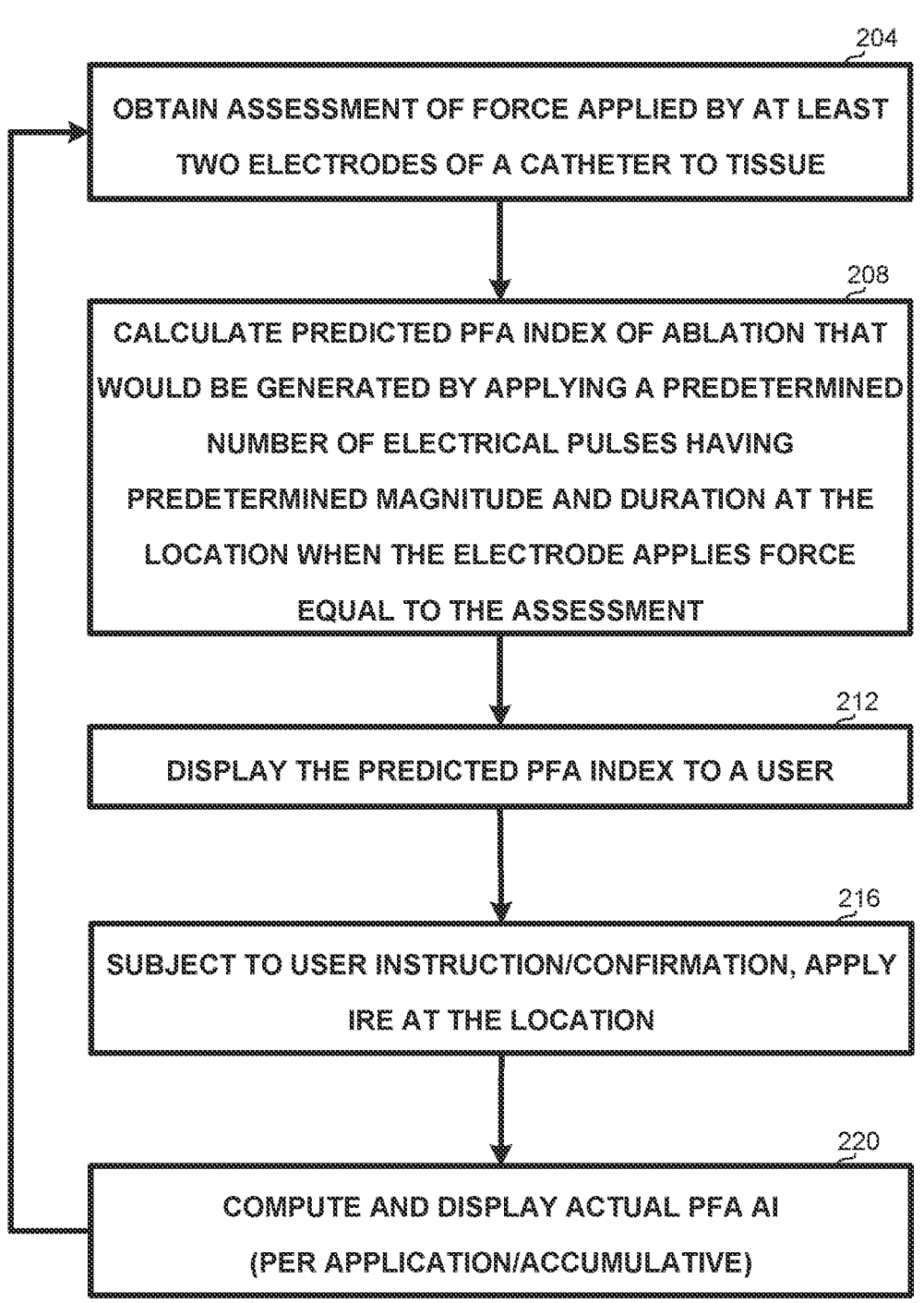

204

OBTAIN ASSESSMENT OF FORCE APPLIED BY AT LEAST
TWO ELECTRODES OF A CATHETER TO TISSUE

208

CALCULATE PREDICTED PFA INDEX OF ABLATION THAT
WOULD BE GENERATED BY APPLYING A PREDETERMINED
NUMBER OF ELECTRICAL PULSES HAVING
PREDETERMINED MAGNITUDE AND DURATION AT THE
LOCATION WHEN THE ELECTRODE APPLIES FORCE
EQUAL TO THE ASSESSMENT

212

DISPLAY THE PREDICTED PFA INDEX TO A USER

216

SUBJECT TO USER INSTRUCTION/CONFIRMATION, APPLY
IRE AT THE LOCATION

220

COMPUTE AND DISPLAY ACTUAL PFA AI
(PER APPLICATION/ACCUMULATIVE)

FIG. 2

METHOD AND SYSTEM FOR CALCULATING AND UTILIZING PFA ABLATION INDEX

FIELD OF THE DISCLOSURE

The present disclosure relates generally to medical devices, and particularly to a system and method for displaying information related to irreversible electroporation of physiological tissues.

BACKGROUND OF THE DISCLOSURE

Arrhythmias may be caused by problems with the electrical conduction system of the heart, and in particular electrical activity in one or more points or areas on a wall of a heart chamber. Atrial fibrillation is an arrhythmia characterized by disorganized signals that make the atria (left and/or right atria) squeeze very fast and in an asynchronous cardiac rhythm.

A common treatment of atrial fibrillation, also referred to as A-fib, is ablation which uses energy to create scars on one or more active areas on the heart wall, in order to block faulty electrical signals that contribute to the disorganized signals and to restore typical heartbeat.

Irreversible electroporation (IRE), also referred to as Pulsed Field Ablation (PFA), is a soft tissue ablation technique that applies, through a probe that is in contact with or in close proximity to the tissue, short pulses of a high amplitude DC signal to generate an electric field that can lead to lethal nanopores in the cell membrane, thus disrupting the cellular homeostasis (internal physical and chemical conditions). Cell death following IRE results from apoptosis (programmed cell death) and not necrosis (cell injury, which results in the destruction of a cell through the action of its own enzymes) as in all other thermal or radiation-based ablation techniques. IRE is commonly used in tumor ablation in regions where precision and conservation of the extracellular matrix, blood flow and nerves are of importance.

An example pulsed field generator and controller to control the PFA pulses or PFA applications are shown and described in US Patent Application US20210186604A1, which is hereby incorporated by reference in its entirety and for all purposes.

BRIEF DESCRIPTION OF THE DRAWINGS

The present disclosure will be more fully understood from the following detailed description of the examples thereof, taken together with the drawings, in which:

FIG. 2 is a flowchart of steps in a method for calculating, displaying and utilizing a predicted PFA index, in accordance with some exemplary embodiments of the disclosure.

DETAILED DESCRIPTION OF EXAMPLES

Figure 1A:
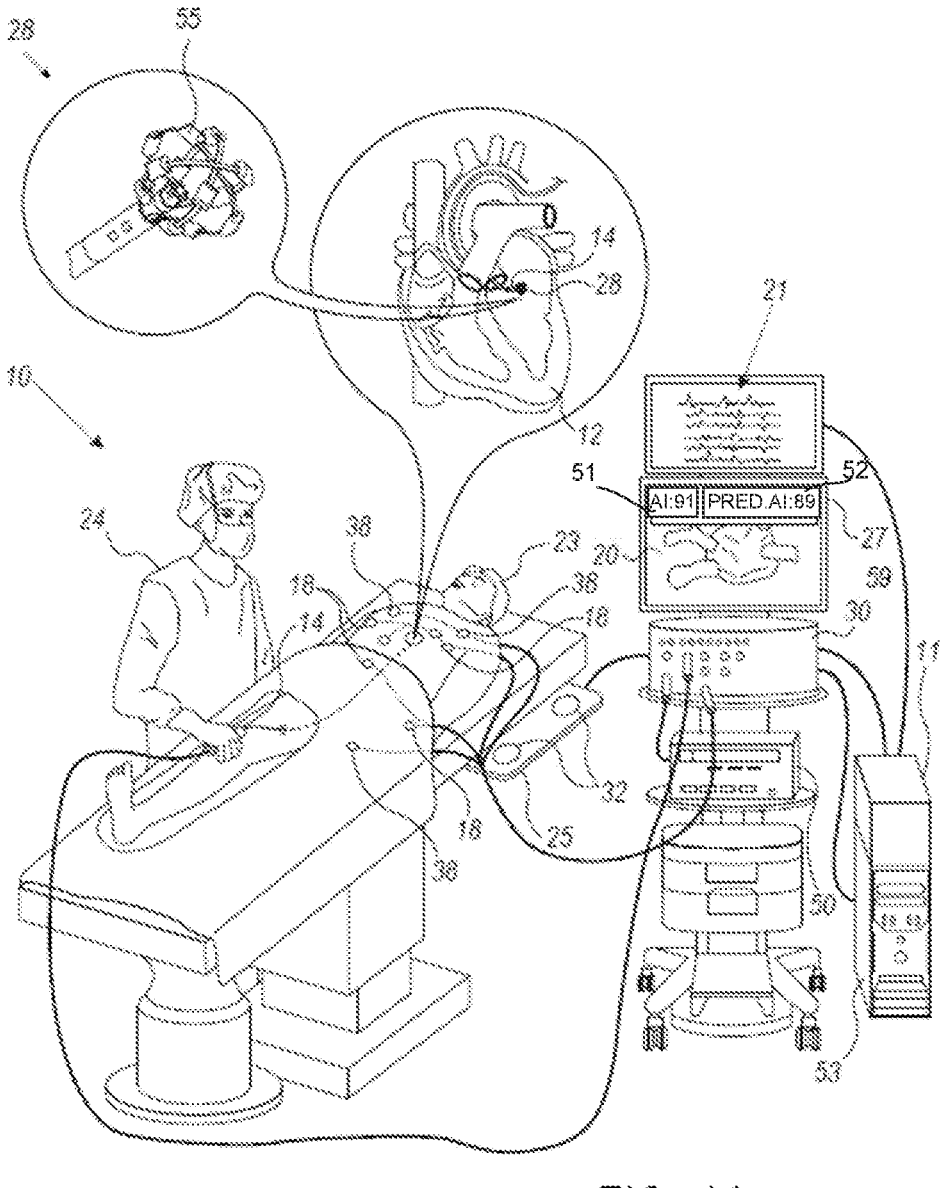
FIG. 1A is a schematic, pictorial illustration of a catheter-based electrophysiological (EP) mapping and ablation system, in accordance with some exemplary embodiments of the disclosure.

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

OVERVIEW

Pulsed Field Ablation (PFA), is a modality where electric fields are generated at a region of interest to induce irreversible electroporation (IRE) to ablate tissue cells by inducing apoptosis (programmed cell death) in the cells. The IRE electric fields are typically delivered by a signal generator in the form of one or more high voltage pulse trains.

PFA may be delivered using a bipolar or monopolar delivery. For bipolar delivery, DC current is delivered between pairs of electrodes that are near the tissue, e.g., typically touching the tissue, to generate a localized electric field near the tissue that is to be ablated and thereby kill tissue cells between the electrodes. For monopolar applications, the current is delivered between an electrode near the tissue e.g., typically touching the tissue and a larger return electrode that may be a patch on the patient's skin or may be a reference electrode on the catheter itself that is immersed in the blood pool or that is touching the tissue at a location remote from a location configured for ablation.

The effectiveness of applying PFA, i.e., the ablation quality, may be estimated and/or rated based on computing a PFA ablation index (AI). The PFA ablation index provides an indication of parameters of lesion created by PFA, e.g., the lesion area and/or depth. The lesion and thus the PFA ablation index may depend on the parameters of the applied pulses, including the contact force applied by the catheter on the heart wall which the present inventors have found to be an important parameter affecting the quality of the caused lesion, and the number of pulses, their frequency, duration and amplitude. In particular, unlike the number, frequency, duration and amplitude of the applied pulses which are fixed, the applied force is controllable by the physician, thereby enabling the physician to control the quality of the lesion caused due to PFA and thus the PFA ablation index.

Optionally, the PFA ablation index may be more specifically dependent on contact force applied by one or more selected electrodes of the catheter. Optionally, the selected electrodes are electrodes that are determined to be touching the heart wall. The PFA ablation index may further depend on the specific location within the heart wall where the ablation is applied, and may be affected, for example, by the type of tissue, its thickness and its morphology.

Typically, ablation is performed by repeated applications of trains of pulses, with a pause, for example of about 1 second, between applications. The AI may be calculated and displayed after each application, by calculating and adding a Delta AI to the cumulative AI for all applications delivered, such that the user can decide whether and how to apply another train of pulses.

Typically, the pulse parameters are predetermined. Thus, the parameters that are typically controllable by the physician applying the ablation are the location and the force to be applied to the heart wall by the electrode. However, a physician may not have a good feel for how much contact force needs to be applied to obtain satisfactory PFA AIs. Thus, by displaying the PFA AI predicted upon a currently applied force, the physician may fine tune the applied force to achieve the desired effect. Moreover, a physician may want to achieve a desired PFA AI and maintain that PFA AI over a lesion formed by multiple ablation sites. Thus, in some example embodiments, a computed and displayed predictive PFA AI may help the physician reach a desired PFA AI and/or achieve a uniform PFA AI over an ablation region formed by multiple ablation sites.

Thus, in accordance with some embodiments of the disclosure, contact force is monitored and a predicted PFA ablation index may be calculated based on the assumption that the physician will maintain that contact force throughout a predefined number of applications. The predicted PFA AI may be displayed to the physician and may provide indication to the physician on how much contact force to apply to achieve a desired PFA AI, e.g., a desired lesion size and/or depth. The predicted PFA displayed may be automatically and continuously updated as the contact force applied by the physician changes.

In some embodiments, the total force applied by the catheter on the heart wall may be measured, wherein the forces applied by one or more electrodes touching the heart wall may contribute to said force. In other embodiments, the separate forces applied by the one or more electrodes may be considered.

The index may be predicted using the same equation that is used to compute an actual PFA AI.

The index may be calculated by integrating the effect of each pulse over the predetermined number of pulses, where it is assumed that during all pulses the force is maintained at the same value as is currently measured.

Based on the prediction, the physician may then decide whether to ablate at the specific location, and whether to do so with the current force being applied on the tissue, or to change the location and/or the applied force.

The predicted PFA ablation index may be displayed to the user continuously or only when the catheter and/or electrodes contact the tissue, and the display may vary as the physician changes the location of the catheter and/or electrodes or the force applied by the catheter and/or the electrode against the heart wall.

System Description

Reference is made to FIG. 1A showing an example catheter-based electrophysiology mapping and ablation system 10. System 10 may include multiple catheters, which are percutaneously inserted by a physician 24 through the vascular system of a patient 23 into a chamber or vascular structure of a heart 12. Typically, a delivery sheath catheter is inserted into the left or right atrium near a desired location in heart 12. Thereafter, one or more catheters may be inserted into the delivery sheath catheter so as to arrive at the desired location in heart 12. The plurality of catheters, including for example catheter 14, may include catheters dedicated for sensing Intracardiac Electrogram (IEGM) signals, catheters dedicated for ablating and/or catheters for both sensing and ablating. Physician 24 may place a distal tip 28 of catheter 14 in contact with the heart wall for obtaining a prediction of a PFA ablation index, or for ablating a target site in heart 12.

Catheter 14 is an exemplary catheter to be used with an irreversible electroporation (IRE) ablation system. Catheter 14 may comprise a distal tip 28. Distal tip 28 may comprise multiple electrodes 55 connected by wires running through catheter 14 to console 30.

Once distal end 28 of catheter 14 is inserted into the patient's body and has reached the target location within heart 12, physician 24 may manipulate catheter 14 to place electrodes 55 disposed over distal tip 28 in contact with the target location, such as the ostium of the pulmonary vein.

In the example described herein, electrodes 55 may be used for IRE ablation of tissue of a left atrium of heart 12 such an ostium tissue of a pulmonary vein in heart 12, by high voltage.

The proximal end of catheter 14 receives energy from IRE ablation energy generator 50 through control console 30. IRE power source 50 may produce but is not limited to, pulsed-field ablation (PFA) energy, including monopolar, bipolar or a combination thereof of high-voltage DC pulses, as may be used to effect irreversible electroporation (IRE). Bipolar pulses may be applied between one or more pairs of electrodes 55. The pairs of electrodes 55 through which the pulses are to be applied may be selected according to the applicable protocol, for achieving uniformity and penetration depth of the IRE field into the tissue, with minimal thermal heating side effects.

Figure 1B:
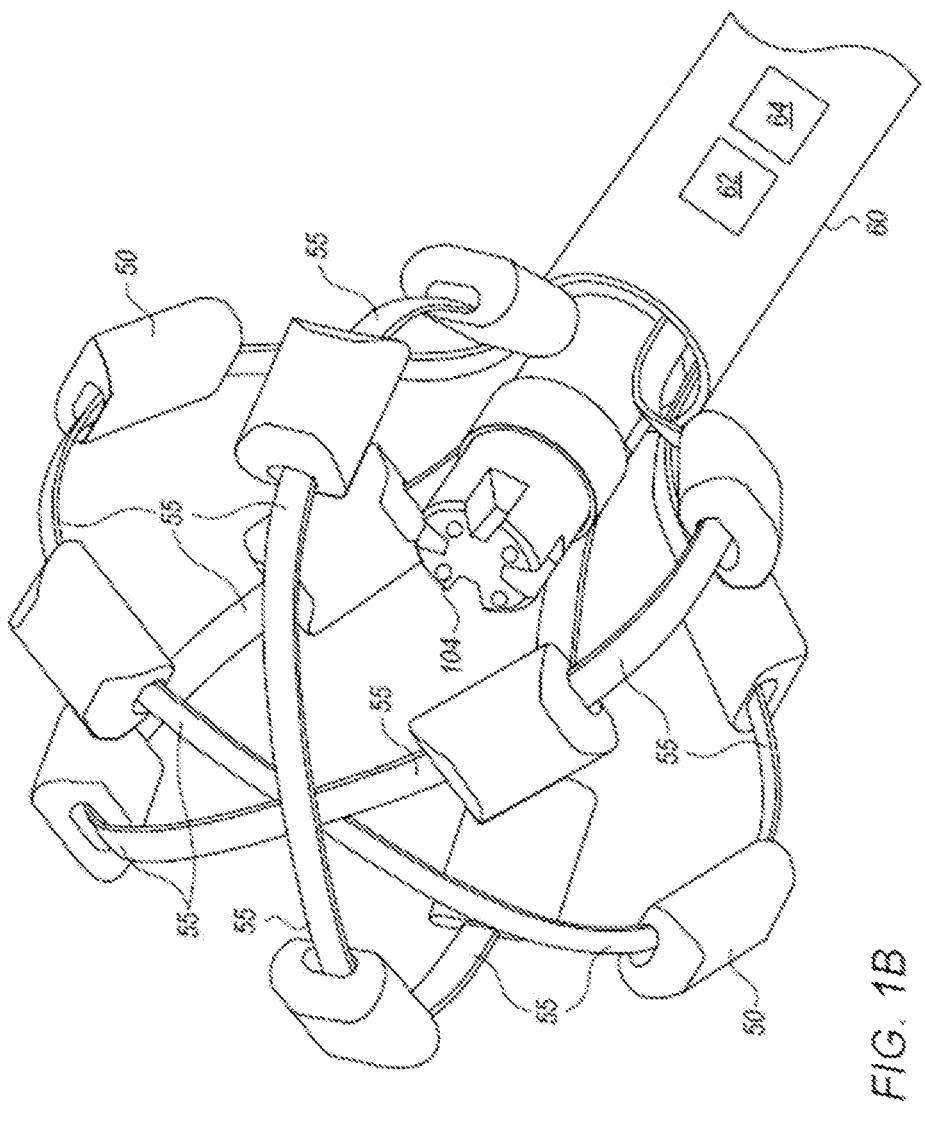
FIG. 1B is a schematic, pictorial illustration of a catheter, in accordance with some exemplary embodiments of the disclosure.

Referring now also to FIG. 1B, showing an enlarged pictorial view of distal tip 28 of catheter 14.

Distal tip 28 comprises a plurality of electrodes 50, positioned over splines 55. In the exemplary embodiment of FIG. 1B, distal tip 28 comprises three splines arranged as a sphere, wherein each spline has four electrodes disposed thereon.

The ends of each splines are coupled to central shaft 60. Central shaft 60 may comprise an irrigation system and one or more irrigation openings 104 for injecting irrigation fluid to the heart.

Central shaft 60 may further comprise a force sensor 62, configured to sense the total force exerted on the heart wall electrodes 55. The force may be calculated as the sum (or average or any other integration) of the forces applied by each of electrodes 55 on the heart wall; the sum (or average or any other integration) of the forces applied by those electrodes 55 that according to the protocol are to receive energy and cause ablation; the maximum force applied by any of electrodes 55 on the heart wall, or the like.

Central shaft 60 may further comprise a position sensor 64 for tracking position and orientation of distal tip 28. Optionally and preferably, the position sensor is a magnetic-based position sensor including three magnetic coils for sensing three-dimensional (3D) position and orientation.

The magnetic based position sensor may be operated together with a location pad 25 including a plurality of magnetic coils 32 configured to generate magnetic fields in a predefined working volume. Real time position of distal tip 28 or any of electrodes 55 of catheter 14 may be tracked based on magnetic fields generated with location pad 25 and sensed by magnetic based position sensor 64. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

System 10 may include one or more electrode patches 38 positioned for skin contact on patient 23 to establish location reference for location pad 25 as well as impedance-based tracking of electrodes 55. For impedance-based tracking, electrical current is directed to electrodes 55 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

The force applied by distal tip 28 on the heart wall, and optionally the location within the heart, may be used to calculate the PFA ablation index once ablation energy has been applied to the tissue. However, the force and optionally the location may also be used for predicting the PFA ablation index before the energy is applied assuming that physician 24 will apply the same amount of force, such that physician 24 may apply the required force at a specific location to achieve a desired lesion and/or a desired PFA AI. The predicted PFA ablation index may be calculated based on the force in the same manner as the actual PFA ablation index is calculated once the energy has been applied.

A recorder 11 may record and display electrograms 21 captured with body surface ECG electrodes 18 and intracardiac electrograms (IEGM) captured with a corresponding catheter. Recorder 11 may include pacing capability for pacing the heart rhythm and/or may be electrically connected to a standalone pacer.

Patient interface unit (PIU) 30 is an interface configured to establish electrical communication between catheters, other electrophysiological equipment, power supply and a workstation 53 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 53 includes memory, processor unit with memory or storage with appropriate operating software stored therein, and user interface capability. Workstation 53 may provide multiple functions, optionally including (1) displaying on display device 27 a current PFA index 51, calculated upon the force and location of catheter 14, and a predicted PFA index 52 (2) modeling the endocardial anatomy in three-dimensions (3D) and rendering the model or anatomical map 20 for display on a display device 27, (3) displaying on display device 27 activation sequences (or other data) compiled from recorded electrograms 21 in representative visual indicia or imagery superimposed on the rendered anatomical map 20, (4) displaying real-time location and orientation of multiple catheters within the heart chamber, and (5) displaying on display device 27 sites of interest such as places where ablation energy has been applied. One commercial product embodying elements of system 10 is available as the CARTO™ 3 System, available from Biosense Webster, Inc., 31A Technology Drive, Irvine, CA 92618.

In some embodiments, the model or anatomical map 20 may indicate thereon the PFA ablation index or a prediction thereof for a plurality of locations within the heart.

In some embodiments, the indices may be displayed for areas where the electrodes have applied force on the heart wall and indicate the PFA ablation index predicted upon the force applied at each such location.

In other embodiments, the indices may be displayed for all areas of the heart wall and indicate the predicted PFA ablation index calculated upon an average predetermined force, such that the physician can choose the best locations. In some embodiments, the average force used for prediction may be a parameter learned per physician, for example the force the physician usually applied during ablation.

Referring now to FIG. 2, showing a flowchart of steps in a method for calculating, displaying and utilizing a predicted PFA index, in accordance with some exemplary embodiments of the disclosure.

On step 204, a force assessment or measurement may be obtained from a force sensor located at the distal end of the shaft and measuring the force at which the physician is pressing the catheter on against a body tissue.

In some embodiments, when assessing the force, the local forces exerted by the electrodes of the electrode pairs that would be activated under the current protocol may be considered. For example, the sum of the forces exerted by the electrodes, the average, the maximum force applied by any of the electrodes or the like.

In other embodiments, the force may be calculated upon the sum, average maximum or any other measure of the forces applied by all electrodes. Optionally, the force is the force sensed on a distal end of the shaft proximal to the location at which the distal end assembly is connected to the shaft.

On step 208, a predicted PFA ablation index may be calculated, which predicts the PFA ablation index that would be obtained by applying a predetermined number of electrical pulses or pulse trains having predetermined magnitude and predetermined duration at the location, when the electrode applies to the tissue amount of force equal to the assessed force.

The predicted PFA ablation index may be calculated using the same calculation that is used to compute the actual PFA AI once ablation has been applied. An important variable in this calculation is the force applied by the catheter on the heart wall, which the physician can affect. The calculation includes other parameters including the following: the number of pulses to be applied and their respective magnitude and duration, in accordance with the applicable protocol which typically predefined; information specific to the patient if available, or generic information based on the general structure of the heart otherwise; and the specific location within the heart and its characteristics, such as the thickness of the tissue at the relevant location, the tissue type, its conductivity, or the like.

The location information may be global to the catheter or specific to each electrode. In the latter case, the predicted PFA ablation index may be combined from the force applied to each active electrode and the characteristics of the specific location at which the electrode contacts the body tissue.

Ablation Index via PFA is described and shown in US Patent Application Publication US20210186604A1, which is incorporated by reference in its entirety for all purposes.

To predict and control ablation treatment, a PFA AI may be computed and displayed to a user. For PFA ablation, a possible scale can correspond to a size S indicating a depth of the lesion, which may depend on, F, P, and T, wherein F is the force applied by the catheter to the tissue, P is the power dissipated during the ablation procedure; and T is the time of the procedure, as derived from the number of repetitions of the pulses and train of pulses. In some embodiments, an estimate of size S may be given by finding an integral over time of an expression comprising functions of F, P, and T.

The estimate may be applied during PFA such that PFA can be halted when a desired lesion size and/or PFA AI is reached.

In an exemplary embodiment of the disclosure the PFA AI may be derived by calculating a summation over the time period of a product of the contact force and the number of repetitions.

The PFA AI may be calculated in accordance with the following formula:

$$PFA\,AI = \sum\nolimits_{n=1}^{N} [AI_n - AI_{n-1}]$$

wherein N equals the number of applications of PFA pulses (hereafter referred to as "PFA applications", and has a predetermined maximum value. It is appreciated that each application of pulses adds to the total PFA AI.

$AI_n$ is an Ablation Index for the $n^{th}$ application of pulses and is equal to the depth of the lesion multiplied by a factor A, with the depth being a logarithmic function of force for the particular application (force(n)) such that:

$$AI_n = A * B_n * \ln(\text{force}(n)) + Cn;$$

and $$AI_{n-1} = A * B_{n-1} * \ln(\text{force}(n)) + C_{n-1}$$

wherein A is a number within a predetermined range,
$B_n$ is a predefined parameter determined by the equation:

$$B_n = B_0 * \ln(n) + B_1$$

where $B_0$ and $B_1$ are predefined constants, and
$C_n$ is a predefined parameter determined by the equation:

$$C_n = C_0 * \exp(C_1 * n)$$

where $C_0$ and $C_1$ are predefined constants.

The A, $B_n$ and $C_n$ values may be determined empirically for each application iteration and calibrated for each type of catheter and type of cardiac structure and given tissue characteristics.

It is noted that $AI_n$ and $AI_{n-1}$ are calculated for each iteration such that the value of $AI_{n-1}$ when used in the $n^{th}$ iteration, is not taken from the previous calculation. The displayed PFA may also be updated accordingly with each application.

The predicted PFA AI may be similarly calculated. However, since it is assumed that the force applied over all applications is constant, the formula is simplified to:

$$\text{Predicted } PFA\,AI = AI_N - AI_1$$

Wherein $$AI_1 = A * B_1 + \ln(\text{force}) + C_1,$$

$$AI_N = A * B_N * \ln(\text{force}) + C_N$$

force is the measured value of the force applied by the catheter at the prediction time and assumed to be fixed throughout all applications, $$B_N = B_0 * \ln(N) + B_1, \text{ and}$$

$$C_N = C_0 * \exp(C_1 * N),$$

In some embodiments, both the PFA AI and the predicted PFA AI may be provided to the user as non-dimensional numbers or range of non-dimensional numbers between a minima and maxima of representing a less than ideal ablation and ideal lesion, respectively. In one example, the ablation index is a non-dimensional scale between two limits, such as 0 and 1000, 250 and 850, or the like.

It is noted that for the actual PFA, $AI_n$ and $AI_{n-1}$ are calculated for each application such that the value of $AI_{n-1}$ when used in the $n^{th}$ iteration, is not taken from the previous calculation. The displayed PFA may also be updated accordingly with each application. The predicted AI, however, is computed for the predefined number of applications based on the instantaneous force as measured, and the predicted AI is the value displayed.

Based on the predicted ablation index the physician can decide for or against ablating at a specific location or repeating the ablation, and/or the physician can decide if more or less contact force is desired during ablation.

On step 212, the predicted PFA ablation index may be displayed to a user of the system, such as a physician, for example as shown in text 51 of FIG. 1. Optionally, the predicted PFA ablation index is displayed alongside the display of an actual PFA ablation index.

Additionally or alternatively, a map of the heart may be updated wherein each of a plurality of locations on the map may be associated with and display predicted PFA indices that have been calculated when the physician brought the catheter to contact with the heart tissue. The map may be color coded, shade coded, pattern coded, or the like.

Additionally or alternatively, a map of the heart may be displayed which shows a generic map of predicted PFA ablation indices in multiple locations, based on the type of tissue and its thickness. The map may display the indices based on generic predetermined force or typical force applied by the physician, as learned from the current session or previous sessions of the physician.

The calculation and the display may be updated every predetermined period of time, such as every second, every 5 seconds, or the like. In alternative embodiments, the calculation and the display may be updated continuously, for example every time the catheter is moved.

On step 216, optionally subject to user's instruction, or subject to confirmation to a displayed notice, the generator may be operated by the user and IRE energy may be supplied to the electrodes in accordance with the applicable protocol, and hence to the tissue. Thus, a predetermined number of pulses of electrical current of predetermined width are provided to the relevant electrodes and hence at the location, to create ablation.

On step 220, subject to the ablation having been performed, the actual PFA ablation index may be computed and displayed. Typically, the actual PFA AI is computed on a per application basis and the cumulative PFA AI is displayed after each application as the ablation is being applied.

In some embodiments, following the application, the actual PFA ablation index may be compared to the predicted value, to obtain at least one difference.

In some embodiments, the comparison results, including the at least one difference, may be used for learning prediction parameters, such that future predictions are more accurate. For example, if the prediction is consistently higher or lower than the actual value, the prediction may be decreased or increased, respectively. In further cases, more complex relationships may be learned between any two or more of the applied force, tissue characteristics, the catheter structure and the applied protocol. The learning may be performed automatically by a processor, manually by a human operator, or in a hybrid manner.

Figure 3:
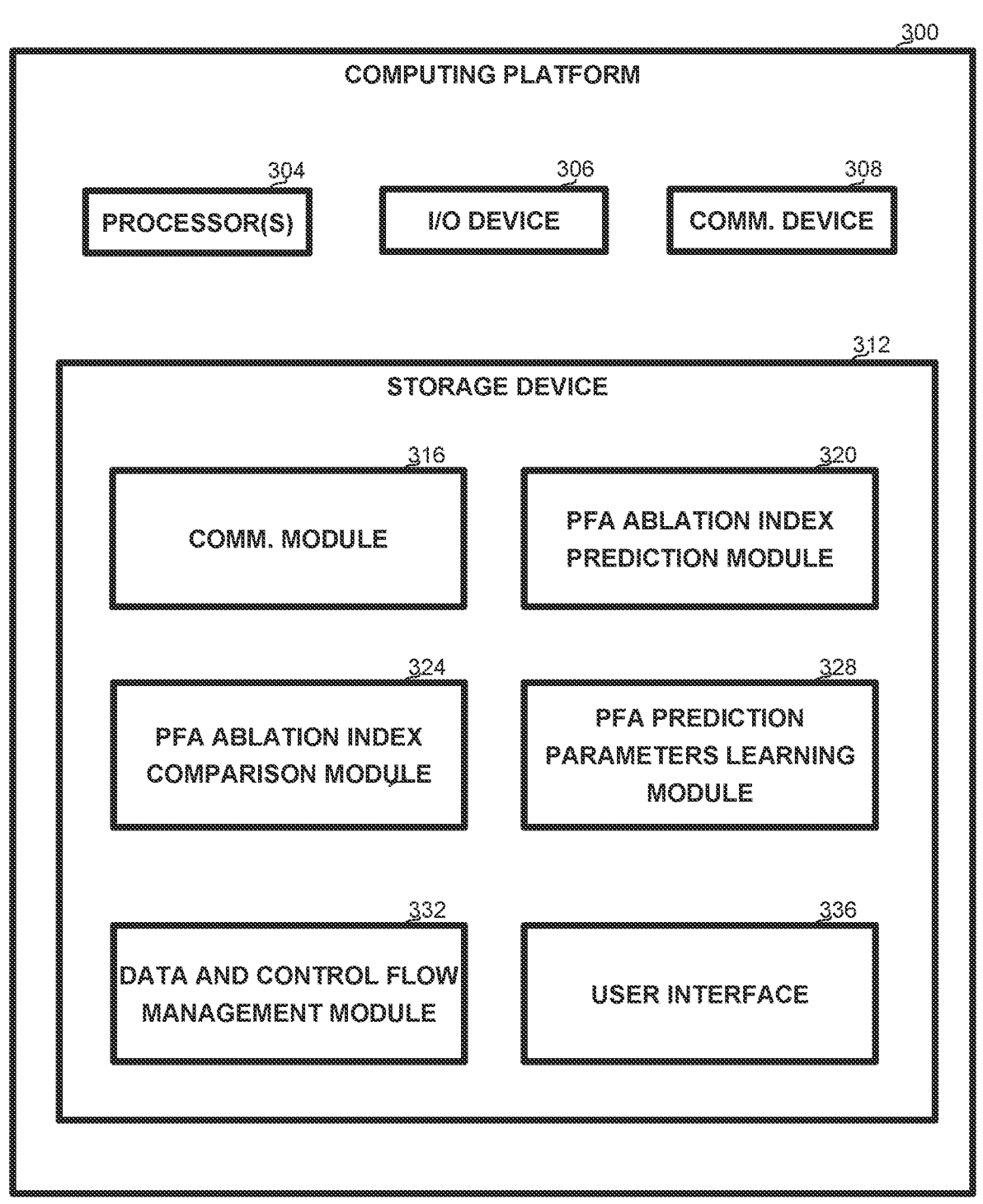
FIG. 3 is a schematic block diagram of a computing platform for calculating, displaying and utilizing a predicted PFA index, in accordance with some exemplary embodiments of the disclosure.

Referring now to FIG. 3, showing a block diagram of a computing platform 300 for calculating, displaying and utilizing a predicted PFA ablation index, in accordance with some exemplary embodiments of the disclosure.

It will be appreciated that computing platform 300 may be embedded within console 30 or workstation 53, but may also be a standalone computing platform or embedded elsewhere and be in operative communication with console 30.

Computing platform 300 may be implemented as one or more computing platforms which may be operatively connected to each other. For example, one or more remote computing platforms, which may be implemented for example on a cloud computer. Other computing platforms may be a part of a computer network of the associated organization. In other embodiments, all the functionality may be provided by one or more computing platforms all being a part of the organization network.

Computing platform 300 may comprise one or more processors 304 located on the same computing platform or not, which may be one or more Central Processing Units (CPU), microprocessors, electronic circuits, Integrated Circuits (IC) or the like. Processor 304 may be configured to provide the required functionality, for example by loading to memory and activating the software modules stored on storage device 312 detailed below.

Computing platform 300 may comprise Input/output (I/O) device 306, such as a display, a pointing device, a keyboard, a touch screen, a speaker, a microphone, or the like. I/O Device 306 may be utilized to receive input from and provide output to a user such as a physician, for example display the predicted PFA ablation index, receive operating instructions, or the like.

Computing platform 300 may comprise a communication device 308 for communicating with other devices or other computing platforms, for example obtaining pressure information from a force sensor, obtaining operation information from the catheterization controller, storing data on remote storage devices, or the like. Communication module 308 may be adapted to interface with any communication channel such as Local Area Network (LAN), Wide Area Network (WAN), cellular network or the like, and use any relevant communication protocol.

Computing platform 300 may comprise a storage device 312, such as a hard disk drive, a Flash disk, a Random Access Memory (RAM), a memory chip, or the like. In some exemplary embodiments, storage device 312 may retain program code operative to cause processor 304 to perform acts associated with any of the modules listed below, or steps of the method of FIG. 2 above. The program code may comprise one or more executable units, such as functions, libraries, standalone programs or the like, adapted to execute instructions as detailed below.

Alternatively or additionally, the provided instructions may be stored on non-transitory tangible computer-readable media, such as magnetic, optical, or electronic memory.

Storage device 312 may comprise communication module 316 for transmitting and receiving data to and from other systems, such as the catheter control system, force sensor, external storage devices, a display system, or the like, through communication device 308. In particular, communication module 316 may be operative in receiving force measurements from one or more force sensors associated with the catheter, for example located at the distal end of the catheter.

Storage device 312 may comprise PFA ablation index prediction module 320 for calculating a predicted index based on the sensed force, the electrode and signal parameters, and optionally the location, as detailed in association with step 208 above.

Storage device 312 may comprise PFA ablation index comparison module 324 for comparing a predict PFA ablation index with an actual PFA ablation index measured at the location post-ablation.

Storage device 312 may comprise PFA prediction parameters learning module 328 for adapting parameters or computations of PFA ablation index prediction module 320, based on the differences between the predicted PFA ablation indices and the actual ones. PFA ablation index prediction module 328 may thus adapt its internal parameters or computations such that future predictions will predict more closely the actual results, in order to enable a physician to take better decisions on where to perform ablation, and how much force to exert during the ablation. Learning the parameters may be performed automatically, manually or a combination thereof.

Storage device 312 may comprise data and control flow management module 332, for activating the modules above in the correct order and with the required input, for example activating PFA prediction parameters learning module 328 after information of predicted PFA ablation index and actual PFA ablation index are available for a plurality of locations.

Storage device 312 may comprise user interface 336, for rendering a display to the user to be displayed over display device 27, such as the predicted PFA ablation index 51, a map of the heart indication ablation indices or predictions thereof, or the like. User interface 336 may also be operative in receiving instructions and operation parameters from controls 32 operated by the user, or the like.

It is appreciated that the steps and modules disclosed above are in addition to the software, hardware, firmware or other modules required for operating the catheter, displaying the catheterization process, performing other calculations such as complex fractionated electrogram (CFE) analysis, generating the heart map, or the like. Further details for methods and systems may be found, for example in U.S. Pat.

Nos. 8,676,305, 9,629,567, incorporated herein by reference in their entirety for any purpose.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture instructions, machine instructions, machine dependent instructions, microcode, firmware instructions, state-setting data, or either source code or object code written in any combination of one or more programming languages, programming languages such as Java, C, C++, Python, or others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

EXAMPLES

Example 1

A method comprising: receiving input from a force sensor on a catheter, the catheter comprising electrodes for ablating a heart of a patient, the catheter placed at a location within the heart; based at least on the received input, calculating a predicted PFA ablation index (PFA AI) of an ablation that would be caused by applying by the catheter force equal to the assessment at the location for a predetermined number of electrical pulses having predetermined magnitude and predetermined duration, wherein said calculation is in accordance with a predefined formula; and displaying the predicted PFA AI to a user of the catheter.

Example 2

The method according to example 1, further comprising: receiving updated input from the force sensor; and repeating said calculating and said displaying for the updated input.

Example 3

The method according to example 1, further comprising displaying an actual PFA AI computed after ablation has been performed with an actual force measured during application, alongside the predicted PFA ablation index.

Example 4

The method according to example 1, wherein said calculation is equal to a calculation of PFA AI once ablation has been applied with a force equal to the assessment.

Example 5

The method according to example 1, wherein the predicted PFA AI calculation is based on the location on the wall of the heart.

Example 6

The method according to example 1, wherein the predicted PFA AI calculation is based on tissue type, tissue thickness, or tissue conductivity of a tissue at the location on the wall of the heart.

Example 7

The method according to example 1, wherein the predicted PFA AI calculation is based on characteristics of the electrodes or applied signals.

Example 8

The method according to example 1, wherein calculating the predicted PFA AI is based on a following formula:

$$\text{Predicted } PFA\ AI = AI_N - AI_1$$

wherein $$AI_1 = A * B_1 * \ln(\text{force}) + C_1$$

$$AI_N = A * B_N * \ln(\text{force}) + C_N$$

N equals a number of applications of PFA pulses,
force is the measured value of the force applied by the catheter at the prediction time and assumed to be fixed throughout all applications, $$B_N = B_0 * \ln(N) + B_1,$$

$$C_N = C_0 * \exp(C_1 * N),$$

A is a number within a predetermined range, and $B_0$, $B_1$, $C_0$ and $C_1$ are predefined constants.

Example 9

The method according to example 8, wherein A, $B_0$, $B_1$, $C_0$ and $C_1$ are determined empirically for each catheter type, and a type of cardiac structure and given tissue characteristics at the location.

Example 10

A computerized apparatus having a processor coupled with a memory unit, the processor being adapted to perform the steps of: receiving input from a force sensor on a catheter, the catheter comprising electrodes for ablating a heart of a patient, the catheter placed at a location within the heart; based at least on the received input, calculating a predicted PFA ablation index (PFA AI) of an ablation that would be caused by applying by the catheter force equal to the assessment at the location for a predetermined number of electrical pulses having predetermined magnitude and predetermined duration, wherein said calculation is in accordance with a predefined formula; and displaying the predicted PFA AI to a user of the catheter.

Example 11

The apparatus according to example 10, wherein the processor is further adapted to perform: receiving updated input from the force sensor; and repeating said calculating and said displaying for the updated input.

Example 12

The apparatus according to example 10, wherein the processor is further adapted to display an actual PFA AI computed after ablation has been performed with an actual force measured during application, alongside the predicted PFA ablation index.

Example 13

The apparatus according to example 10, wherein said calculation is equal to a calculation of PFA AI once ablation has been applied with a force equal to the assessment.

Example 14

The apparatus according to example 10, wherein the predicted PFA AI calculation is based on the location on the wall of the heart.

Example 15

The apparatus according to example 10, wherein the predicted PFA AI calculation is based on tissue type, tissue thickness, or tissue conductivity of a tissue at the location on the wall of the heart.

Example 16

The apparatus according to example 10, wherein the predicted PFA AI calculation is based on characteristics of the electrodes or applied signals.

Example 17

The apparatus according to example 10, wherein calculating the predicted PFA AI is based on a following formula:

$$\text{Predicted } PFA\, AI = AI_N - AI_1$$

wherein $$AI_1 = A * B_1 * \ln(\text{force}) + C_1$$

$$AI_N = A * B_N * \ln(\text{force}) + C_N$$

N equals a number of applications of PFA pulses, force is the measured value of the force applied by the catheter at the prediction time and assumed to be fixed throughout all applications, $$B_N = B_0 * \ln(N) + B_1,$$

$$C_N = C_0 * \exp(C_1 * N),$$

A is a number within a predetermined range, and $B_0$, $B_1$, $C_0$ and $C_1$ are predefined constants.

Example 18

The apparatus according to example 10, wherein A, $B_0$, $B_1$, $C_0$ and $C_1$ are determined empirically for each catheter type, and a type of cardiac structure and given tissue characteristics at the location.

Example 19

A computer program product comprising a non-transitory computer readable medium retaining program instructions, which instructions when read by a processor, cause the processor to perform: receiving input from a force sensor on a catheter, the catheter comprising electrodes for ablating a heart of a patient, the catheter placed at a location within the heart; based at least on the received input, calculating a predicted PFA ablation index (PFA AI) of an ablation that would be caused by applying by the catheter force equal to the assessment at the location for a predetermined number of electrical pulses having predetermined magnitude and predetermined duration, wherein said calculation is in accordance with a predefined formula; and displaying the predicted PFA AI to a user of the catheter.

Example 20

The computer program product according to example 19, wherein calculating the predicted PFA AI is based on a following formula:

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A method comprising:

receiving input from a force sensor disposed on a catheter placed at a location along a wall of a heart of a patient during a procedure, the catheter further comprising electrodes for ablating the heart of the patient;

determining an instant force currently being applied by the catheter at the location based on the input received from the force sensor;

calculating a predicted pulsed field ablation (PFA) ablation index (PFA AI) of an ablation that would be caused by applying, by the catheter, a force equal to the instant force currently being applied at the location for a predetermined number of electrical pulses having a predetermined magnitude and predetermined duration, wherein the predetermined number of electrical pulses is delivered over a predefined number of applications, and wherein said calculation is in accordance with a predefined formula:

$$\text{Predicted } PFA\, AI = AI_N - AI_1$$

wherein, $$AI_1 = A * B_1 + \ln(\text{force}) + C_1$$

$$AI_N = A * B_N * \ln(\text{force}) + C_N$$

N is the predefined number of applications, force is a measured value of the instant force which is assumed to be fixed throughout the predefined number of applications, $B_N$ is a predefined parameter, $C_N$ is a predefined parameter, A is a number within a predetermined range, and $B_1$ and $C_1$ are predefined constants; and displaying, via a display device, the predicted PFA AI to a user of the catheter during the procedure.

2. The method of claim 1, further comprising:

receiving updated input from the force sensor; and repeating said calculating and said displaying for the updated input.

3. The method of claim 1, further comprising:

determining an actual PFA AI computed after ablation has been performed with an actual force measured over the predefined number of applications, wherein the actual force varies over the predefined number of applications; and displaying, via the display device, the actual PFA AI alongside the predicted PFA AI.

4. The method of claim 1, wherein the predicted PFA AI is based on the location on the wall of the heart.

5. The method of claim 1, wherein the predicted PFA AI is based on tissue type, tissue thickness, or tissue conductivity of a tissue at the location on the wall of the heart.

6. The method of claim 1, wherein:

the predefined parameter $B_N$ is determined according to a formula the predefined parameter $C_N$ is determined according to a formula $$B_N = B_0 * \ln(N) + B_1,$$

$$C_N = C_0 * \exp(C_1 * N),$$

and $B_0$ and $C_0$ are predefined constants.

7. The method of claim 6, wherein A, $B_0$, $B_1$, $C_0$ and $C_1$ are determined empirically based on catheter type and cardiac structure at the location.

8. A system, comprising:

a catheter, the catheter comprising a force sensor and electrodes for ablating a heart of a patient, the catheter configured to be placed at a location along a wall of the heart of the patient; and a computerized apparatus in communication with the catheter, the computerized apparatus having a processor coupled with a memory unit, the processor being adapted to perform the steps of:

receiving input, during a procedure, from the force sensor on a of the catheter placed at the location along the wall of the heart;

determining an instant force currently being applied by the catheter at the location based at least on the received input, calculating a predicted pulsed field ablation (PFA) ablation index (PFA AI) of an ablation that would be caused by applying, by the catheter, a force equal to the instant force currently being applied at the location for a predetermined number of electrical pulses having a predetermined magnitude and predetermined duration, wherein the predetermined number of electrical pulses is delivered over a predefined number of applications, and wherein said calculation is in accordance with a predefined formula:

$$\text{Predicted PFA AI} = AI_N - AI_1,$$

wherein, $$AI_1 = A*B_1*\ln(\text{force}) + C_1,$$

$$AI_N = A*BN*\ln(\text{force}) + C_N,$$

N is the predetermined number of applications, force is a measured value of the instant force which is assumed to be fixed throughout the predefined number of applications, B is a predefined parameter, $C_N$ is a predefined parameter, A is a number within a predetermined range, and $B_1$ and $C_1$ are predefined constants; and displaying, via a display device, the predicted PFA AI to a user of the catheter during the procedure.

9. The apparatus system of claim 8, wherein the processor is further adapted to perform the steps of:

receiving updated input from the force sensor; and repeating said calculating and said displaying for the updated input.

10. The system of claim 8, wherein the processor is further adapted to perform the steps of:

determining an actual PFA AI computed after ablation has been performed with an actual force measured over the predefined number of applications; and displaying, via the display device, the actual PFA AI alongside the predicted PFA AI.

11. The system of claim 8, wherein the predicted PFA AI is based on the location on the wall of the heart.

12. The system of claim 8, wherein the predicted PFA AI is based on tissue type, tissue thickness, or tissue conductivity of a tissue at the location on the wall of the heart.

13. The system of claim 8, wherein:

the predefined parameter $B_N$ is determined according to a formula $B_N = B_0*\ln(N) + B_1$, the predefined parameter $C_N$ is determined according to a formula $C_N = C_0*\exp(C_1*N)$, and $B_0$ and $C_0$ are predefined constants.

14. The system of claim 13, wherein A, $B_0$, $B_1$, $C_0$ and $C_1$ are determined empirically based on catheter type and cardiac structure at the location.

\* \* \* \* \*